United States Patent
Lorraine et al.

(10) Patent No.: US 7,966,883 B2
(45) Date of Patent: Jun. 28, 2011

(54) NON-DESTRUCTIVE INSPECTION USING LASER-ULTRASOUND AND INFRARED THERMOGRAPHY

(75) Inventors: Peter William Lorraine, Niskayuna, NY (US); Donald Robert Howard, Troy, NY (US); Harry Israel Ringermacher, Delanson, NY (US); Marc Dubois, Keller, TX (US); Thomas E. Drake, Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 1238 days.

(21) Appl. No.: 11/567,444

(22) Filed: Dec. 6, 2006

(65) Prior Publication Data
US 2008/0291465 A1 Nov. 27, 2008

(51) Int. Cl.
*G01N 29/04* (2006.01)
*G01J 9/02* (2006.01)
*G02F 1/01* (2006.01)

(52) U.S. Cl. .............. 73/601; 73/602; 73/632; 356/502; 250/330

(58) Field of Classification Search .................. 73/601, 73/602, 632; 356/432, 502; 250/330
See application file for complete search history.

(56) References Cited

U.S. PATENT DOCUMENTS

| | | | |
|---|---|---|---|
| 5,608,166 A * | 3/1997 | Monchalin et al. ............. 73/657 |
| 6,122,060 A * | 9/2000 | Drake, Jr. ..................... 356/502 |
| 6,367,969 B1 | 4/2002 | Ringermacher et al. |
| 6,516,084 B2 * | 2/2003 | Shepard ........................ 382/141 |
| 6,633,384 B1 * | 10/2003 | Drake et al. .................. 356/432 |
| 6,696,692 B1 | 2/2004 | Pepper |
| 6,813,951 B2 * | 11/2004 | Blouin et al. .................... 73/643 |
| 7,038,790 B2 * | 5/2006 | Drake, Jr. ..................... 356/502 |
| 7,365,330 B1 * | 4/2008 | Sun ............................ 250/341.6 |
| 7,516,663 B2 * | 4/2009 | Ringermacher et al. ........ 73/601 |
| 7,549,789 B2 * | 6/2009 | Tralshawala et al. ........... 374/43 |
| 7,561,281 B2 * | 7/2009 | Drake, Jr. ..................... 356/502 |
| 7,591,583 B2 * | 9/2009 | Foes et al. ......................... 374/5 |
| 7,604,331 B2 * | 10/2009 | Saito .............................. 347/71 |
| 7,605,924 B2 * | 10/2009 | Howard et al. ............... 356/502 |
| 2003/0106376 A1 | 6/2003 | Shirzad et al. |
| 2004/0149021 A1 | 8/2004 | Kessler et al. |

FOREIGN PATENT DOCUMENTS

EP 1582867 A2 10/2005

OTHER PUBLICATIONS

International Search Report, Application No. PCT/US2007/025228, dated May 19, 2008.

\* cited by examiner

*Primary Examiner* — Jacques M Saint Surin
(74) *Attorney, Agent, or Firm* — Bracewell & Giuliani LLP

(57) ABSTRACT

An inspection system is provided to examine internal structures of a target material. This inspection system includes a generation laser, an ultrasonic detection system, a thermal imaging system, and a processor/control module. The generation laser produces a pulsed laser beam that is operable to induce ultrasonic displacements and thermal transients at the target material. The ultrasonic detection system detects ultrasonic surface displacements at the target material. The thermal imaging system detects thermal transients at the target material. The processor analyzes both detected ultrasonic displacements and thermal imagery of the target material to yield information about the target material's internal structure.

25 Claims, 7 Drawing Sheets

NON-DESTRUCTIVE INSPECTION USING LASER-ULTRASOUND AND INFRARED THERMOGRAPHY

TECHNICAL FIELD OF THE INVENTION

The present invention relates non destructive testing, and more particularly, to the use of thermal imaging and ultrasonic testing to inspect the internal structures of materials.

BACKGROUND OF THE INVENTION

In recent years, the use of advanced composite structures has experienced tremendous growth in the aerospace, automotive and many other commercial industries. While composite materials offer significant improvements in performance, they require strict quality control procedures in both the manufacturing processes and after the materials are in service in finished products. Specifically, non-destructive evaluation (NDE) methods must assess the structural integrity of composite materials. Proper assessment demands the ability to detect inclusions, delaminations and porosities both at the near surface region and deep internal region.

Various methods and apparatuses have been proposed to assess the structural integrity of composite structures. One solution uses an ultrasonic source to generate ultrasonic surface displacements in target materials. The ultrasonic surface displacements are then measured and analyzed. The source of the ultrasound may be a pulsed generation laser beam directed at the target. Laser light from a separate detection laser illuminates the ultrasonic surface displacements and is scattered by the work piece surface. Then collection optics collect the scattered laser energy. The collection optics are coupled to an interferometer or other device, and data about the structural integrity of the composite structure can be obtained through analysis of the scattered laser energy. Laser ultrasound has been shown to be very effective for the inspection of parts during the manufacturing process.

Typically, a laser source produces sound by thermal expansion at a localized spot on the surface while a probe laser beam, coupled to an interferometer, detects surface displacements or velocity. The thermal expansion due to the absorption of the generation laser produces a displacement that is demodulated by the laser-ultrasound detection system resulting in a pulse at the beginning of the laser-ultrasound signal. This echo is commonly called surface echo. The surface echo may mask any echo produced by a defect near the sample surface. The duration of the surface echo depends on the generation laser pulse duration and on the frequency bandwidth of the detection system. Typically, with a CO2 generation laser and a confocal Fabry-Perot for detection, the surface echo might last up to a few microseconds. Thus any defect that would produce an echo during that time might be masked. For this reasons Laser-ultrasound inspection is sensitive to deep internal defects and less sensitive to near-surface defect.

Transient infrared (IR) thermography, another NDE method, does not efficiently allow for the inspection of polymer-matrix composites due to its insensitivity to defects deeper than a few mm's in polymer-matrix parts.

SUMMARY OF THE INVENTION

Embodiments of the present invention are directed to systems and methods that substantially address the above identified needs and other needs as well. The embodiments of the present invention are further described in the following description and claims. Advantages and features of embodiments of the present invention may become apparent from the description, accompanying drawings and claims.

Embodiments of the present invention combine laser ultrasound and thermal imaging techniques to substantially address the above identified needs and other needs as well. Laser-ultrasound generation techniques may be used to provide a transient heat source. Thus, transient infrared (IR) thermography may be combined with laser ultrasound to provide a more complete non-destructive inspection of polymer-matrix parts (i.e. composite materials).

One embodiment provides an inspection system to examine near surface and deep internal structures of target material. This inspection system includes a generation lasers an ultrasonic detection system, a thermal imaging system, and a processor/control module. The generation laser produces a pulsed laser beam that is operable to induce both ultrasonic displacements and thermal transients at the target material. The ultrasonic detection system detects ultrasonic surface displacements at the target material. The thermal imaging system detects thermal transients at the target material. The processor/controller analyzes and correlates both detected ultrasonic displacements and thermal imagery of the target material to yield information about the target material's near surface and deep internal structure.

Another embodiment provides a method of inspecting the internal structures of a target. This method involves inducing both ultrasonic displacements and thermal transients at the target material. These ultrasonic displacements and thermal transients may be produced using a single pulsed generation laser beam. The ultrasonic displacements and the thermal transients caused by the generation laser beam directed at a surface of the target may be detected and analyzed. Generation and analysis may involve synchronization and correlation of both ultrasonic information and thermal information to yield a more complete understanding about the structure of the target. Analyzing ultrasonic displacements for example may yield information about deep internal structures within the composite material. Thermal imagery may yield information about year surface internal structures of the composite material. Correlating the ultrasonic information and thermal information results in a better understanding of the overall internal structure of the target.

Yet another embodiment provides a composite material inspection system. This composite material inspection system includes a generation laser to generate a pulsed laser beam that induces ultrasonic displacements and thermal transients at the composite material. An ultrasonic detection system is provided to detect the ultrasonic surface displacements at the composite material. A thermal imaging system is provided to detect thermal transients at the composite material. The control module may match thermal imaging frame acquisition to a pulse rate of the generation laser beam. A processor is provided to analyze and correlate the detected ultrasonic displacements and thermal imagery in order to yield information about the overall internal structure of the target.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGURES, like numerals being used to refer to like and corresponding parts of the various drawings.

Embodiments of the present invention combine laser ultrasound and thermal imaging techniques to provide a more complete non-destructive inspection of target materials such as but not limited to polymer-matrix parts (i.e. composite materials). One embodiment provides an inspection system operable to examine internal structures of the target material. This inspection system includes a generation laser, an ultrasonic detection system, a thermal imaging system, and a processor/control module. The generation laser produces a pulsed laser beam operable to induce both ultrasonic displacements and thermal transients at the target material. The ultrasonic detection system detects ultrasonic surface displacements at the target material. The thermal imaging system detects thermal transients at the target material. The processor analyzes and correlates both detected ultrasonic displacements and thermal imagery of the target material to yield information about the target material's overall internal structure. Embodiments of the present invention provide for faster inspection rates, improved system reliability, and lower operation costs.

Figure 1:
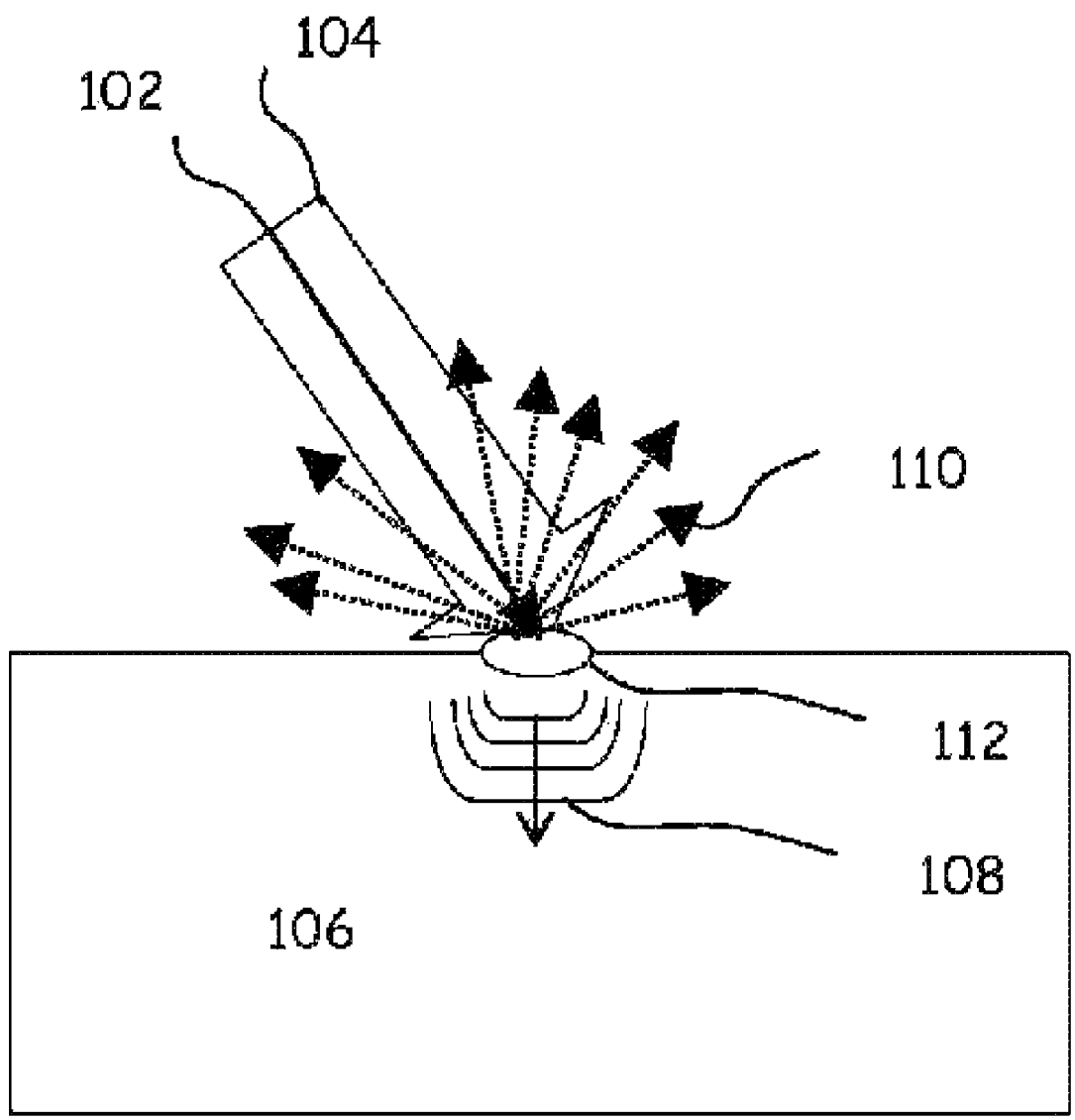
FIG. 1 illustrates the use of generation laser beam and a detection laser beam to generate and detect laser ultrasonic displacements and thermal transients in accordance with or embodiments of the present invention.

FIG. 1 illustrates the use of generation laser beam and a detection laser beam to generate and detect laser ultrasonic displacements and thermal transients in accordance with embodiments of the present invention. Laser beam 102 generates ultrasound and thermal transients while illumination (detection) laser beam 104 detects the ultrasound at a target 106, such as a composite material under test. As shown, these lasers may be coaxially applied to target 106. Generation laser beam 102 causes thermo-elastic expansion 112 in target 106 that results in the formation of ultrasonic deformations or waves 108. Deformations or ultrasonic waves 108 propagate in target 106 and modulate, scatter and reflect detection laser beam 104 to produce phase-modulated light 110 directed away from target 106 which is collected and processed to obtain information describing the internal structure of target 106.

Figure 2:
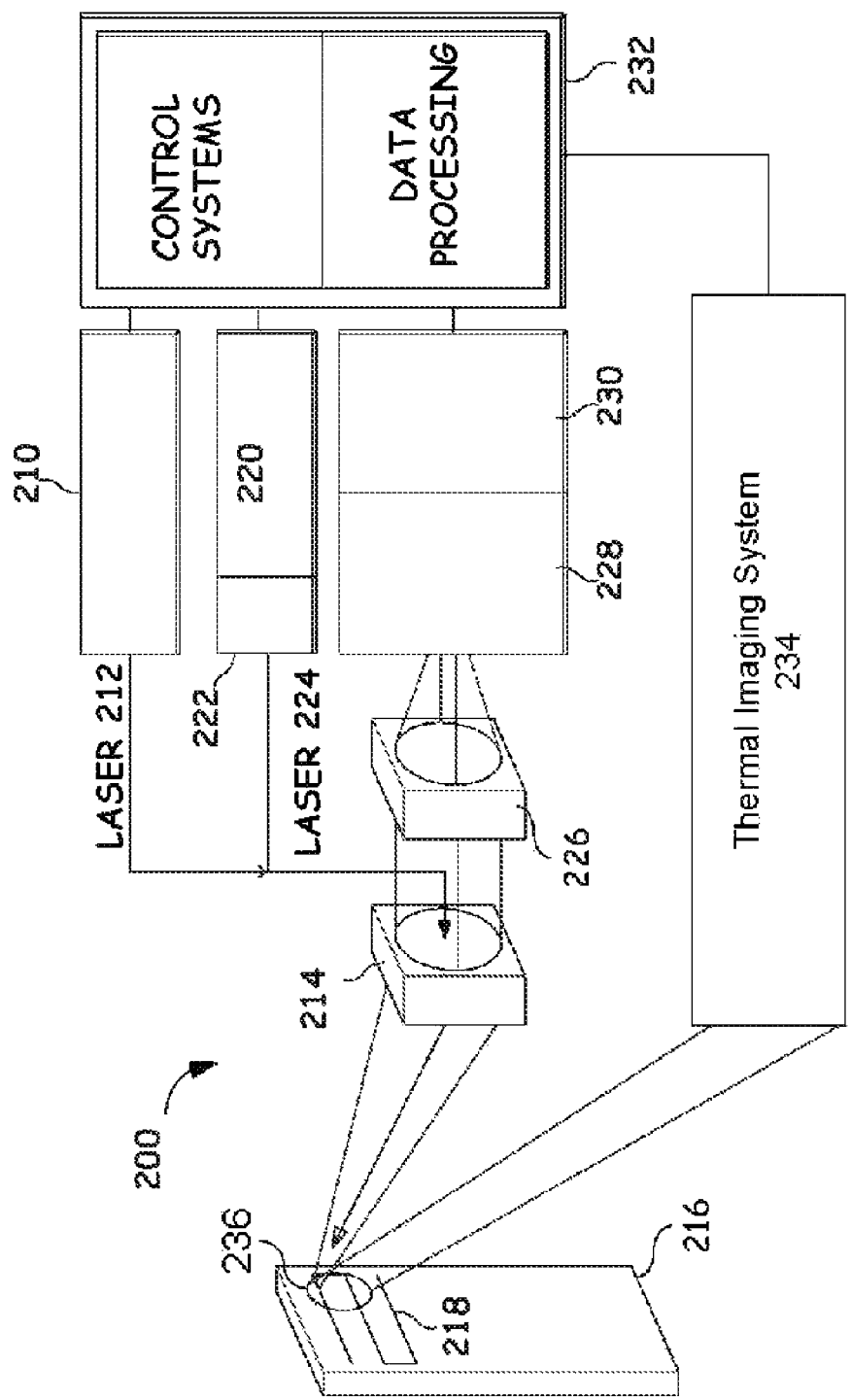
FIG. 2 provides a block diagram to show the basic components of laser ultrasound/thermal imaging system.

FIG. 2 provides a block diagram with the basic components for performing ultrasonic laser testing and infrared (IR) thermography. Generation laser 210 produces generation laser beam 212 which optical assembly 214 directs to target 216. As shown, optical assembly 214 includes a scanner or other like mechanism that moves laser beam 212 along a scan or test plan 218. Optical assembly 214 may include visual cameras, depth cameras, IR cameras, range detectors, narrowband cameras or other like optical sensors known to those having skill in the art. These optical sensors each may require calibrations prior to performing an inspection. This calibration verifies the ability of the system to integrate information gathered by various sensors. Generation laser 210 produces an ultrasonic wave 108 and a thermal transient within target 216. Thermal imaging system 232 captures thermal images of the target. These images are processed to yield information about near surface internal structures of target 216. This process will be described in further detail with reference to FIG. 3 and following.

Thermo-elastic expansion 112 producing ultrasonic wave 108 and thermal transient are the result of the composite material absorbing the generation laser beam. Composite material 216 readily absorbs generation laser beam 212 without ablating or breaking down. Higher powered generation lasers are not necessarily preferred to overcome signal-to-noise ratio (SNR) issues as these can result in ablation of material at the surface of the workpiece, potentially damaging the component. In other embodiments, depending on the material being tested, some ablation may be acceptable in order to increase the SNR of the detected signal. Generation laser beam 212 has appropriate pulse duration, power, and frequency to induce ultrasonic surface deformations and appropriate thermal transients. For example, a transverse-excited atmospheric (TEA) $CO_2$ laser can produce a 10.6 micron wavelength beam for a 100 nanosecond pulse width. The power of the laser must be sufficient to deliver, for examples a 0.25 joule pulse to the target, which may require a 100 watt laser operating at a 400 Hz pulse repetition rate. Generation laser beam 212 is absorbed as heat into the target surface thereby causing thermo-elastic expansion without ablation.

Detection laser 220 operating in pulsed mode or CW mode does not induce ultrasonic displacements. For examples an Nd:YAG laser can be used. The power of this laser must be sufficient to deliver, for example, a 100 milli-joule, 100 micro-second pulse, which may require a one kilo-watt (KW) laser. Detection laser 220 generates detection laser beam 222. Detection laser 220 includes or optically couples to filtering mechanism 224 to remove noise from detection laser beam 224. Optical assembly 214 directs detection laser beam 224 to the surface of composite material 216 which scatters and/or reflects detection laser beam 224. Resultant phase modulated light is collected by collection optics 226. As shown here, scattered and/or reflected detection laser light travels back through optical assembly 214. Optional optical processor 228 and interferometer 230 process the phase modulated light to produce a signal containing information representative of the ultrasonic displacements at the surface of composite material 216. Data processing and control system 232 coordinates operation of the laser ultrasound system components and thermal imagery components to yield information about internal structures of the target.

Data processing and control system 232 may be a single processing device or a plurality of processing devices. Such a processing device may be a microprocessor, micro-controller, digital signal processors microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 232 executes, operational instructions corresponding to at least some of the steps and/or functions as will be illustrated.

Figure 3:
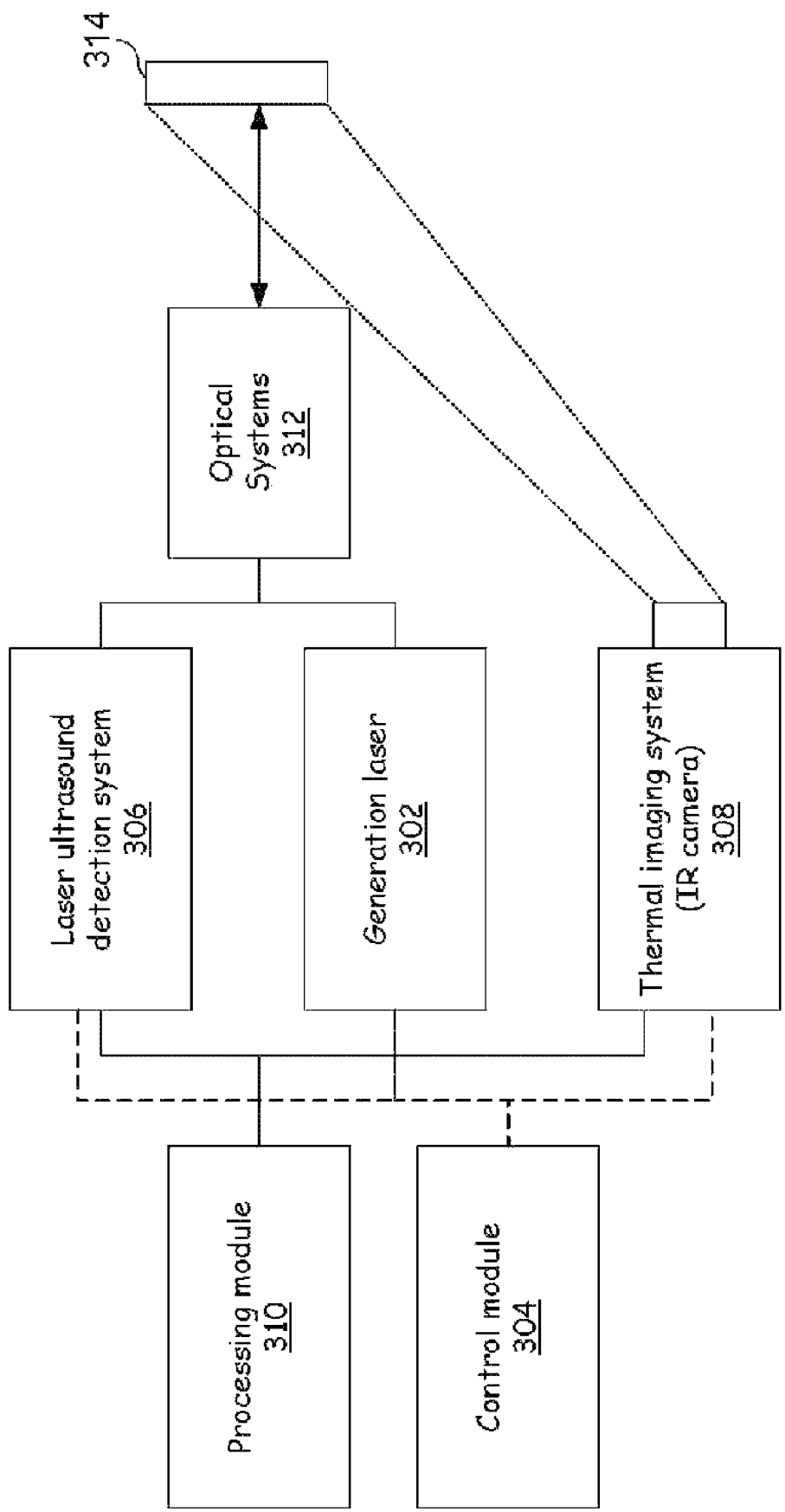
FIG. 3 provides a block diagram or functional diagram of a laser ultrasound and IR imaging system in accordance with embodiments of the present invention.

FIG. 3 provides a block or functional diagram of a laser ultrasound and IR imaging system 300 in accordance with embodiments of the present invention. Laser ultrasound and IR imaging system 300 includes a generation laser 302, a control module 304, a laser ultrasound detection system 306, a thermal imaging system 308, a processing module 310, and optical system 312. Generation laser 302 produces a generation laser beam which is directed by optical systems 312 to a target 314 made of materials such as but not limited to composite materials wherein ultrasonic displacements are induced as discussed above. Laser ultrasound detection system 30G generates a detection laser beam which is directed by optical systems 312 to target 314 wherein ultrasonic displacements at the surface of target 314 cause the detection laser beam to be phase modulated. The detection laser beam is scattered by the surface of the target. Optical systems 312 also collect this scattered phase modulated light. The laser ultrasound detection system 306 processes the collected phase modulated light in order to develop a signal containing information about the ultrasonic displacements. This signal is provided to processing module 310.

Generation laser 302 also creates a thermal transient for thermographic measurements of target 314. A thermal imaging system such an IR camera 308 acquires thermal images or frames of the thermal transients within target 314. An image is acquired for each generation laser pulse. Additional images may be acquired at predetermined times after each generation pulse. These different images are processed to produce a thermographic inspection of the complete area inspected by laser-ultrasound.

The thermographic results complement the laser-ultrasound results and provide in this manner a more complete and more reliable inspection. Transient IR thermography does not by itself provide for the efficient inspection of composite parts such as polymer matrix composites. Transient IR thermography is sensitive only to the top surface of the composite parts because it is a low thermal conductivity on the polymer matrix. Thus, IR thermography cannot be used to identify to detect and identify deep defects within a polymer matrix or composite part.

Laser ultrasound and IR imaging system 300 incorporates both laser ultrasound which provides a deep internal inspection system and thermal imaging to address near surface inspection of target 314. This addresses problems associated with the fact that laser ultrasound inspection may be less sensitive to near surface defects. By combining these two techniques a more complete non-destructive inspection of a composite part or material is possible than was possible when only using laser ultrasound or IR thermography.

Figure 4:
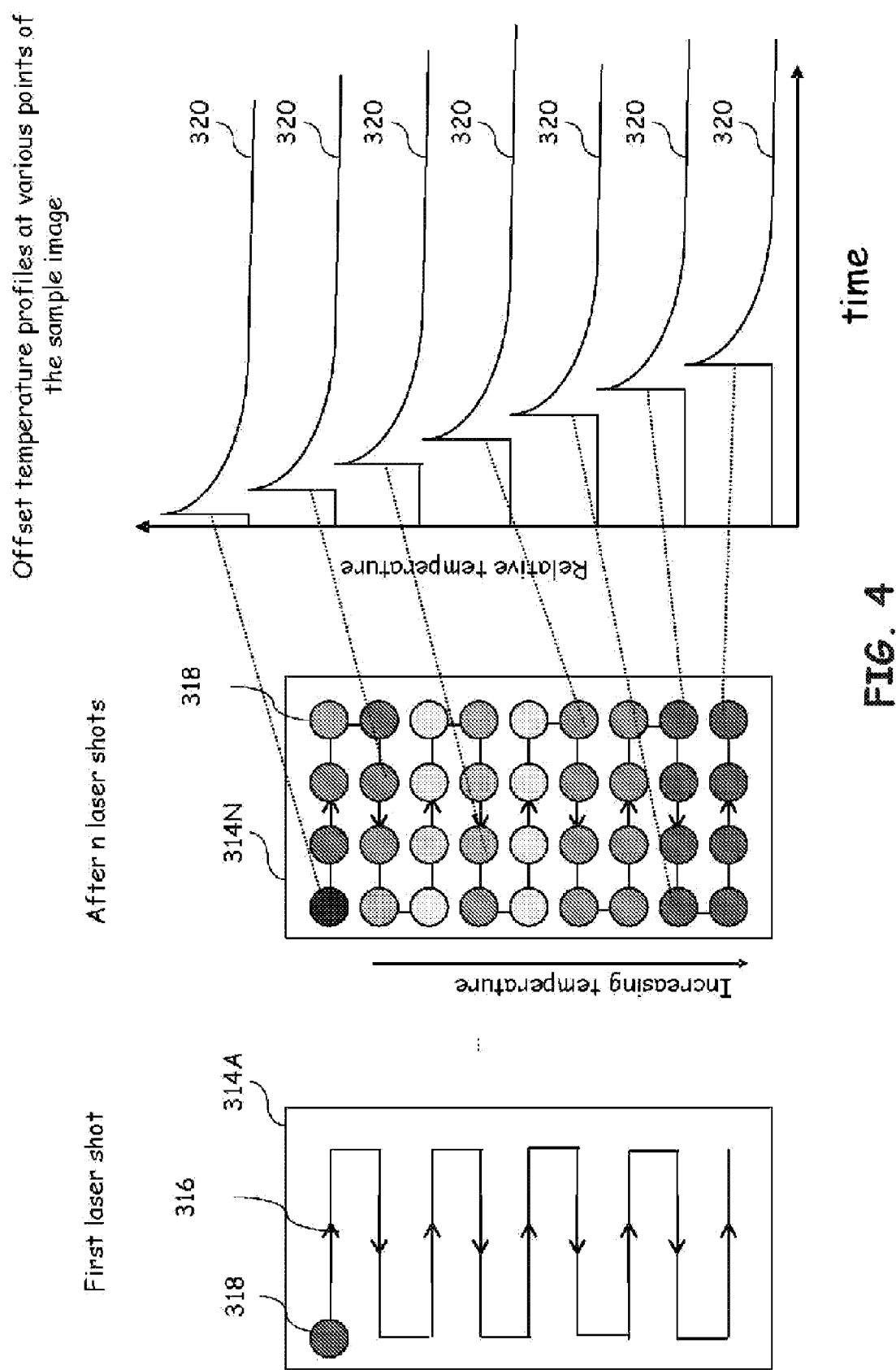
FIG. 4 describes the processing of IR images used to gather information about the near surface internal structure of target in accordance with embodiments of the present invention.
Figure 5:
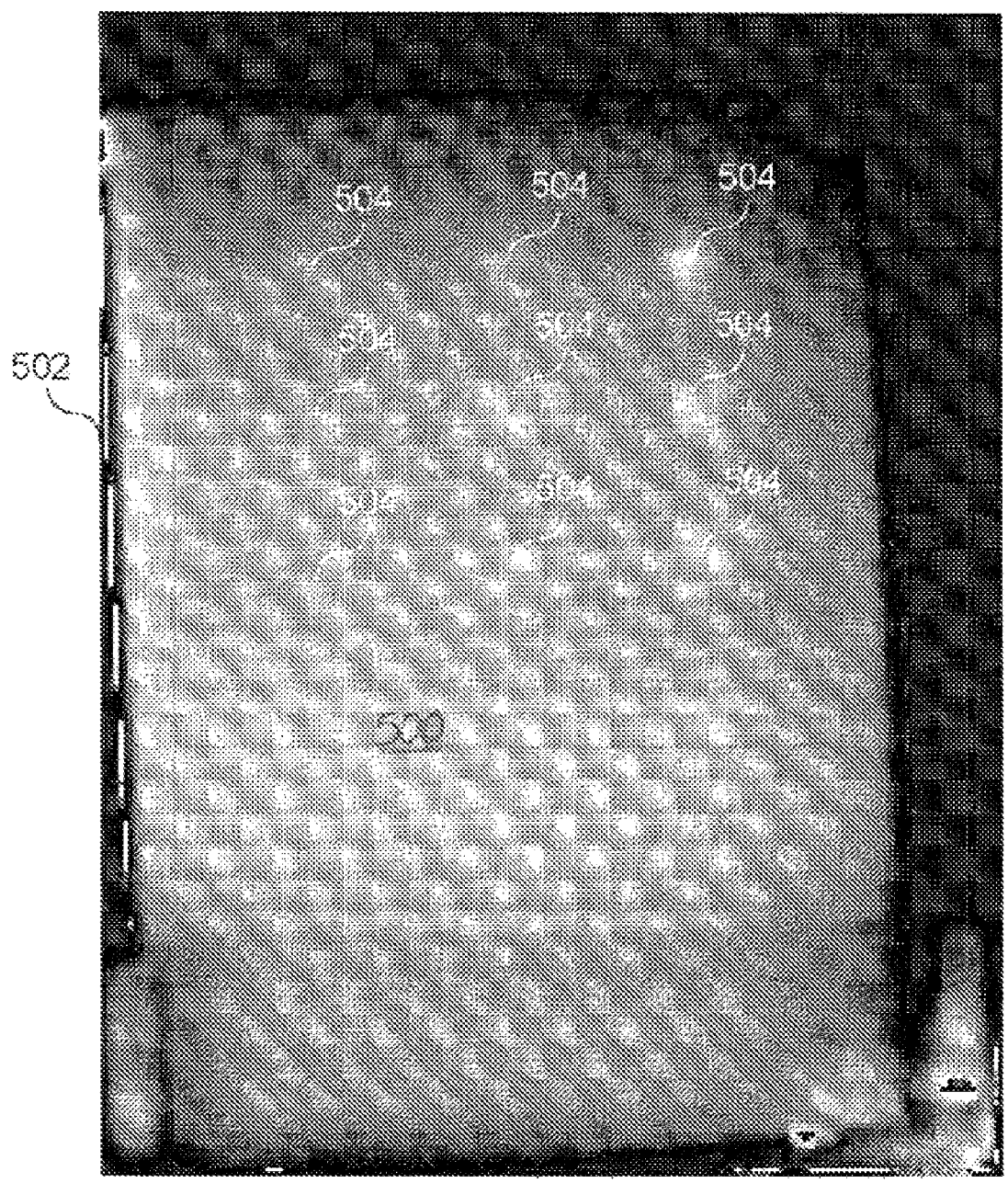
FIG. 5 shows the infrared results obtained by scanning a pulsed CO2 laser beam on a polymer plate with flat-bottom holes in accordance with embodiments of the present invention.

FIG. 4 describes the processing of IR images to gather information about the internal structure of target 314. A thermal image may be gathered after each or predetermined amount of time after the generation laser beam has been fired. As the generation laser beam is fired or pulsed at target 314A the generation laser beam will be scanned along scan path 316. Points 318 at which the generation laser beam is directed will each have a thermal transient 320. Target 314N shows the scanning of path 316 by repeatedly illuminating target 314 with generation laser beam and collecting numerous thermal images. These thermal transients may be used to determine the thermal properties associated with the target material. For example a quantitative thermal wall thickness may be determined by analyzing thermal imagery over time at the target. This may be presented in the form of a synthetic visual image as is illustrated in FIG. 5. This processing approach analyzes infrared images (more specifically temperature variations as a function of time within the different images are analyzed). A relative temperature variation curve is built from all the IR images for each point of the IR camera.

Another embodiment may provide a scanned IR thermography technique to inspect materials for near surface defects. This allows the peak thermal load of the target to be limited in that only a small portion of the target is heated at any one time. Such a system uses a scanned laser to induce thermal transients.

FIG. 5 shows the infrared results obtained by scanning a pulsed $CO_2$ laser beam on a polymer plate with flat-bottom holes. The defects in the target 502 clearly appear in the gray scale image 500. Image 500 includes various points 504 within material 502. This image may be generated using an imaging method such as that described in U.S. Pat. No. 6,367,969 entitled "Synthetic reference thermal imaging method," which is incorporated by reference for all purposes. IR transient thermography analysis approaches may be used to accurately measure the thickness of a target and provide a visual coded display indicative of its cross-sectional thickness over a desired area of the target.

Basically, IR transient thermography use of an inflection point in a temperature-time (T-t) response analysis of the surface of a rapidly heated target, preferably obtained from "front-side" IR camera observations. This inflection point occurs relatively early in the T-t response and is essentially independent of lateral heat loss mechanisms. (Such considerations may be of particular relevance, for example, when working with metals since, due to the high thermal conductivity of metals, the thermal response of a metal target is fairly quick and, consequently, the time available for obtaining thermal data measurements is usually short). The inflection point is extracted from thermal data acquired over a predetermined time period from successive IR camera image frames. Preferably, this time period is at least somewhat longer than an anticipated characteristic time based on an estimation of the thickness of the target being evaluated.

Thermal reference data is computed for each (x,y) pixel location of the imaged target and then used to determine contrast as a function of time for each pixel. A computer system controls the imaging system, records and analyzes surface temperature data acquired via the IR camera, and provides a color or gray pattern-keyed image that accurately corresponds to thickness of the target. This information may be merged with laser ultrasound data to produce a more detailed internal picture of the target.

The acquisition of surface temperature data is initiated by firing the generation laser to illuminate and heat a portion of the surface of the target. Thermal image frames are then recorded over a period of time after each generation laser pulse and the recorded images used to develop a temperature-time (T-t) history, such as that associated with thermal transients 320 of FIG. 4.

Heat flow analysis of the T-t history is then conducted for each pixel in the acquired image frames to determine the thickness of the target at each resolution element location. Conventionally, analysis of transient heat flow through solid portions of a target requires determining a characteristic time required for a "pulse" of thermal energy to penetrate the target at a first surface, reflect off an opposite surface and return to the first surface. Since this characteristic time is related to the distance between the two surfaces, it can be used to determine the thickness of the target between the two surfaces at a desired point. A contrast-versus-time curve is determined for each (x,y) pixel location corresponding to each resolution element of the target surface.

Figure 6:
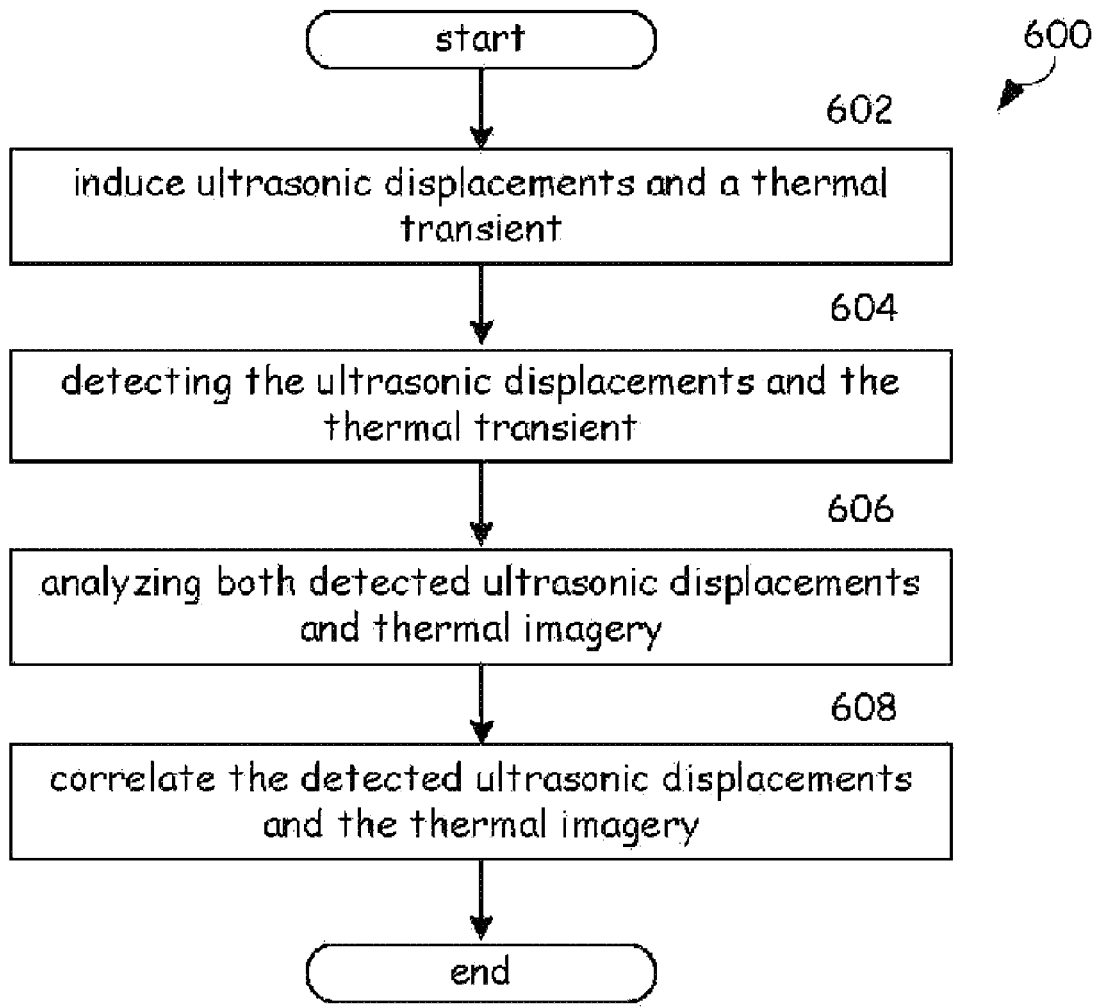
FIG. 6 provides a logic flow diagram in accordance with one or more embodiments of the present invention.

FIG. 6 provides a logic flow diagram describing a method to inspect materials such as but not limited to composite materials in accordance with embodiments of the present invention. Operations 600 apply both laser ultrasound techniques and thermal imaging or infrared thermography techniques in order to inspect and examine the internal structure of a material to be tested. Operations 600 begin in step 602 where ultrasonic displacements and thermal transients are induced in a target material. These may both be done using a generation laser beam associated with a laser ultrasound system. This generation laser beam when directed to the surface of the target material generates both ultrasonic displacements and a thermal transient as discussed with reference to FIGS. 1 and 4. In Step 604 the ultrasonic displacements and thermal transients are detected. The ultrasonic displacements may be detected using an ultrasound system such as but not limited to a laser ultrasound system. The thermal transient may be detected by acquiring thermal imagery of the target material. As discussed previously the generation of the thermal transient and ultrasound may be synchronized or correlated. This information may be used to match the results of analysis performed in step 606. In step 606 both the detected ultrasonic displacements and thermal imagery are analyzed. The detected ultrasonic displacements will provide information regarding the deep internal structures of the target material while the thermal imagery of the thermal transients may be processed to determine near surface structures within the target material. Because the ultrasonic displacements and thermal transients are initiated by the same generation laser beam this information may be used to easily correlate the detected ultrasonic displacements and thermal imagery. This allows in step 608 a detailed composite understanding of both the near surface and deep internal structures of the target material to be realized.

Correlation may be done in part by applying a time stamp to thermal images that are acquired. Also the thermal imaging acquisition frame rate may be matched to the pulse rate of the generation laser beam. Thermography allows a synthetic image for other representation to be determined of the target material. This may involve the determination of a quantitative thermal thickness arrived at by analyzing the thermal imagery. A change in the quantitative thermal wall thickness may indicate a near surface flaw in the target material at the point where the unexpected change in the quantitative thermal wall thickness occurs. This information may be visualized by a contrast display where an abrupt change in contrast indicates a discontinuity or change in the quantitative thermal wall thickness.

Figure 7:
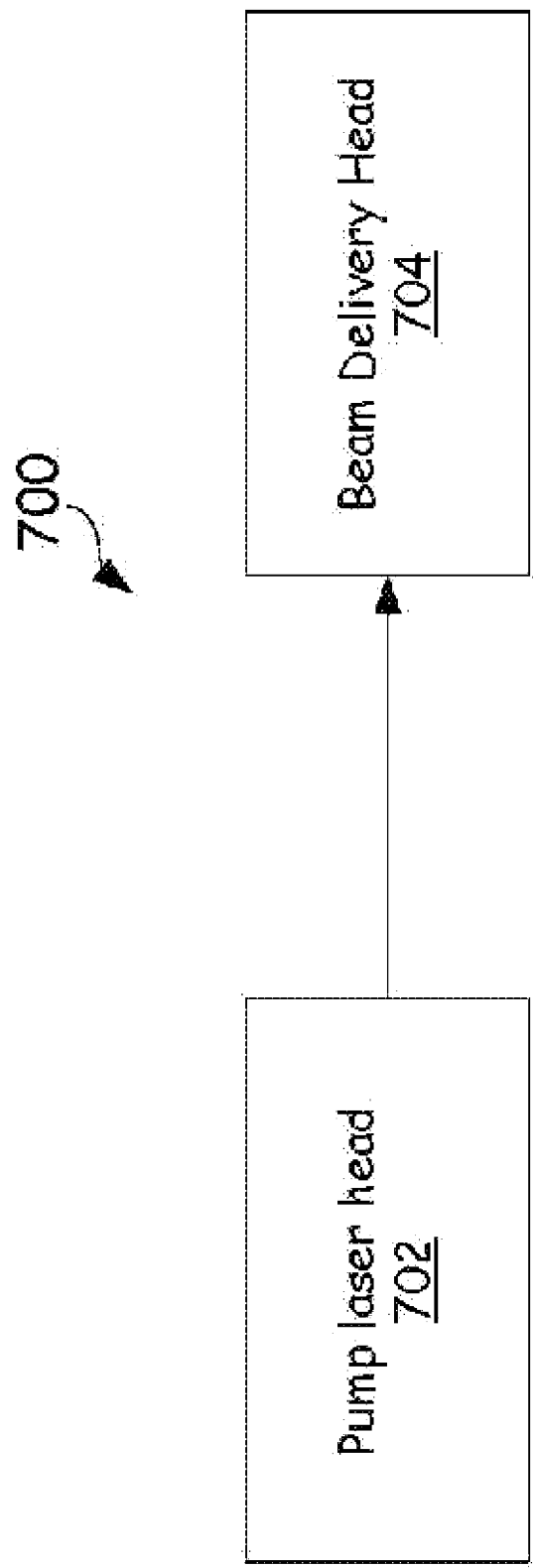
FIG. 7 depicts a block diagram of a generation laser operable to generate ultrasonic displacements and thermal transients in accordance with embodiments of the present invention.

The generation laser beam may be a mid-IR ultrasound generation laser. Such a generation laser provides a compact, high-average power mid-IR laser for ultrasound and thermal transient generation. As shown in FIG. 7, the generation laser 700 includes a pump laser head 702, having a fiber laser therein, fiber coupled to a generation laser head 704. Using fiber lasers allows the laser pump to be located remotely from generation laser head 704. The pump laser head may be coupled via optical fiber 702 to the generation laser head 704.

Locating the pump laser head 702 meters away from generation laser beam delivery head 704 allows a compact mid-IR generation laser head that reduces the overall payload and the stability requirements for robotic systems used to deliver the generation laser beam and acquire thermal images. Only a compact and light-weight module containing the generation laser beam delivery head and an IR camera is required to be mounted within the inspection head of the robotic system. This allows the deployment of a mid-IR laser source using smaller robots. Thus, new composite inspection opportunities are created for in-field composite NDE using portable laser ultrasound systems and IR thermography systems. These approaches are discussed in U.S. patent application Ser. No. 11/458,377, assigned to the assignee of the present application, and entitled "FIBER LASER TO GENERATE ULTRASOUND" which is hereby incorporated for all purposes.

In summary, the embodiments of the present invention provide an inspection system operable to examine internal structures of a target material. This inspection system includes a generation laser, an ultrasonic detection system, a thermal imaging system, and a processor/control module. The generation laser produces a pulsed laser beam that is operable to induce ultrasonic displacements and thermal transients at the target material. The ultrasonic detection system detects ultrasonic surface displacements at the target material. The thermal imaging system detects thermal transients at the target material. The processor analyzes both detected ultrasonic displacements and thermal imagery of the target material to yield information about the target material's internal structure.

As one of average skill in the art will appreciate, the term "substantially" or "approximately", as may be used herein provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component element, circuit, or module does not modify the information of a signal but may adjust its current level, voltage level, and/or power level. As one of average skill in the art will also appreciate, interred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A method to inspect a targets comprising:
   a. using a generation laser beam to produce ultrasonic displacements on the target;
   b. using the generation laser beam to produce time varying thermal transients in the target;
   c. detecting the ultrasonic displacements at the target;
   d. detecting the thermal transients in the target by thermally imaging the target at predetermined times after steps (a) and (b); and e. analyzing both detected ultrasonic displacements at the target and thermal imagery of the target yields information about the target.

2. The method of claim 1, wherein: the target comprises a composite material;
analyzing detected ultrasonic displacements yields information about a deep internal structure of the composite material; and
analyzing thermal imagery at the target yields information about a near surface internal structure of the composite material.

3. The method of claim 2, further comprising correlating information about the deep internal structure of the composite material and the near surface internal structure of the composite material.

4. The method of claim 1, further comprising correlating the detected ultrasonic displacements and the thermal imagery.

5. The method of claim 1, wherein detecting the ultrasonic displacements and the thermal transient at the target further comprises:
matching thermal imaging to a pulse rate of the generation laser beam.

6. The method of claim 1, wherein detecting the ultrasonic displacements and the thermal transient at the target further comprises:
matching thermal imaging frame rate to a pulse rate of the generation laser beam.

7. The method of claim 1, wherein a field of view of the thermal image encompasses a scan plan of the generation laser beam.

8. The method of claim 1, wherein a quantitative thermal wall thickness is determined by analyzing thermal imagery at the target.

9. The method of claim 8, wherein an unexpected change in the quantitative thermal wall thickness indicates a flaw in the target at the unexpected change.

10. The method of claim 1, wherein analyzing thermal imagery at the target comprises infrared (IR) transient thermography.

11. The method of claim 1, further comprising:
generating a detection laser beam;
directing the detection laser beam to the surface of the target;
scattering the detection laser beam at the surface of the target to produce light phase-modulated by ultrasonic surface displacements;
collecting the phase modulated light;
processing the phase modulated light to obtain data representative of the ultrasonic surface displacements at the surface; and
collecting the data with the information to analyze structures within the target.

12. An inspection system operable to inspect an internal structure of a target comprising:
a generation laser operable to generate a pulsed laser beam operable to induce ultrasonic displacements in the target and thermal transients at the target that have a varying temperature over time;
an ultrasonic detection system operable to detect the ultrasonic surface displacements at the target;
a thermal imaging system operable to detect the thermal transient at the target over a period of time;
a processor operable to analyze both detected ultrasonic displacements at the target and thermal imagery of the target to yield information about the internal structure of the target.

13. The inspection system of claim 12, wherein the ultrasonic detection system comprises:
a detection laser operable to generate a detection laser beam operable to illuminate the ultrasonic surface displacements at the target;
collection optics for collecting light phase-modulated by ultrasonic surface displacements from the detection laser beam scattered at the target surface;
an interferometer to process the phase modulated light and generate at least one output signal; and
a processing unit to process the at least one output signal to obtain data representative of the ultrasonic surface displacements at the target.

14. The inspection system of claim 12, wherein the thermal imaging system comprises an infrared (IR) transient thermography system.

15. The inspection system of claim 14, wherein the IR transient thermography system comprises an IR sensitive camera operable to acquire image frames of the target illuminated by the generation laser beam.

16. The inspection system of claim 15, wherein image frames of the target comprise an array of pixels and are assigned a frame number that corresponds to elapsed time, wherein a quantitative thermal wall thickness is determined by analyzing sequential frames of thermal imagery.

17. The inspection system of claim 15, wherein the processing unit correlates the detected ultrasonic displacements and the thermal imagery.

18. The inspection system of claim 15, further comprising a control module operable to match thermal imaging frame acquisition to a pulse rate of the generation laser beam.

19. The inspection system of claim 15, wherein:
the target comprises a composite material; and
the processing unit:
analyzes detected ultrasonic displacements to yield information about a deep internal structure of the composite material;
analyzes thermal imagery at the target to yield information about a near surface internal structure of the composite material; and
correlates information about the deep internal structure of the composite material and the near surface internal structure of the composite material.

20. A large area composite inspection system, comprising:
a generation laser operable to generate a pulsed laser beam operable to induce ultrasonic displacements in a composite material and thermal transients that are defined by a variation in temperature at a location in the composite material irradiated by the pulsed laser beam;
an ultrasonic detection system operable to detect the ultrasonic surface displacements at the composite material;
a thermal imaging system operable to detect the time varying thermal transient at the composite material:
a control module operable to match thermal imaging frame acquisition to a pulse rate of the generation laser beam;
a processor operable to:
analyze both detected ultrasonic displacements at the composite material and thermal imagery of the target to yield information about the internal structure of the target.

21. The inspection system of claim 20, wherein the processing unit analyzes:
analyzes detected ultrasonic displacements to yield information about a deep internal structure of the composite material;

analyzes thermal imagery at the target to yield information about a near surface internal structure of the composite material; and correlates information about the deep internal structure of the composite material and the near surface internal structure of the composite material.

22. The inspection system of claim 20, wherein the ultrasonic detection system comprises:

a detection laser operable to generate a detection laser beam operable to illuminate the ultrasonic surface displacements at the target;

collection optics for collecting light phase-modulated by ultrasonic surface displacements from the detection laser beam scattered at the target surface;

an interferometer to process the phase modulated light and generate at least one output signal; and a processing unit to process the at least one output signal to obtain data representative of the ultrasonic surface displacements at the target.

23. The inspection system of claim 20, wherein the thermal imaging system comprises an infrared (IR) transient thermography system.

24. The inspection system of claim 23, wherein the IR transient thermography system comprises an IR sensitive camera operable to acquire image frames of the target illuminated by the generation laser beam.

25. The inspection system of claim 20, wherein image frames comprise an array of pixels and are assigned a frame number that corresponds to elapsed time, wherein a quantitative thermal gall thickness is determined by analyzing sequential frames of thermal imagery.

* * * * *